US010813592B2

(12) United States Patent
Massey et al.

(10) Patent No.: US 10,813,592 B2
(45) Date of Patent: *Oct. 27, 2020

(54) PHYSIOLOGICAL SENSOR HISTORY BACKFILL SYSTEM AND METHOD

(71) Applicant: Medtronic MiniMed, Inc., Northridge, CA (US)

(72) Inventors: Linda Massey, Winnetka, CA (US); Thomas Collins, Palos Verdes Estates, CA (US); David Lewinski, Chagrin Falls, OH (US); Linda Torres, Moorpark, CA (US); Yongbo Wang, San Marino, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 383 days.

This patent is subject to a terminal disclaimer.

(21) Appl. No.: 15/887,981

(22) Filed: Feb. 3, 2018

(65) Prior Publication Data

US 2018/0153475 A1 Jun. 7, 2018

Related U.S. Application Data

(63) Continuation of application No. 14/304,686, filed on Jun. 13, 2014, now Pat. No. 9,901,305.

(51) Int. Cl.
*A61B 5/145* (2006.01)
*A61B 5/01* (2006.01)
(Continued)

(52) U.S. Cl.
CPC ........ *A61B 5/7207* (2013.01); *A61B 5/14532* (2013.01); *A61B 5/4839* (2013.01);
(Continued)

(58) Field of Classification Search
CPC . A61B 5/7207; A61B 5/14532; A61B 5/4839; A61B 5/0002; A61B 5/01;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

*Primary Examiner* — Navin Natnithithadha
(74) *Attorney, Agent, or Firm* — Lorenz & Kopf, LLC

(57) ABSTRACT

A physiological sensor history backfill system and method including a method of sensor history backfill for a local base device operable to wirelessly communicate with a physiological sensor connected to a patient, the method including: obtaining physiological readings for the patient at a predetermined interval; storing the physiological readings at the physiological sensor as sensor physiological readings; storing the physiological readings at the local base device as historic physiological readings; obtaining a current physiological reading for the patient; transmitting the current physiological reading to the local base device in a current reading message; detecting a record gap in the historic physiological readings between the current physiological reading and the historic physiological readings; and filling the record gap in the historic physiological readings with sensor physiological readings from the physiological sensor when the current reading message does not include the sensor physiological readings to fill the record gap.

19 Claims, 4 Drawing Sheets

(51) Int. Cl.
*A61B 5/021* (2006.01)
*A61B 5/024* (2006.01)
*A61B 5/0402* (2006.01)
*A61B 5/0476* (2006.01)
*A61B 5/00* (2006.01)
*A61B 5/11* (2006.01)

(52) U.S. Cl.
CPC ............... *A61B 5/0002* (2013.01); *A61B 5/01* (2013.01); *A61B 5/021* (2013.01); *A61B 5/024* (2013.01); *A61B 5/0402* (2013.01); *A61B 5/0476* (2013.01); *A61B 5/1118* (2013.01); *A61B 5/14542* (2013.01); *A61B 5/6801* (2013.01); *A61B 5/6898* (2013.01)

(58) Field of Classification Search
CPC ....... A61B 5/021; A61B 5/024; A61B 5/0402; A61B 5/0476; A61B 5/1118; A61B 5/14542; A61B 5/6801; A61B 5/6898
USPC .......................................... 600/309, 345–366
See application file for complete search history.

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,665,065 A | 9/1997 | Colman et al. | |
| 5,694,941 A * | 12/1997 | Riley | A61B 5/0444 600/509 |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,483,967 B2 * | 7/2013 | Harper | A61B 5/14532 702/19 |
| 8,755,938 B2 * | 6/2014 | Weinert | G06F 19/3456 700/266 |
| 8,775,120 B2 * | 7/2014 | Molettiere | A61B 5/0002 702/160 |
| 8,849,610 B2 * | 9/2014 | Molettiere | A61B 5/1112 702/160 |
| 9,901,305 B2 * | 2/2018 | Massey | A61B 5/7207 |
| 2007/0123819 A1 | 5/2007 | Mernoe et al. | |
| 2010/0160861 A1 | 6/2010 | Causey, III et al. | |
| 2010/0280782 A1 * | 11/2010 | Harper | A61B 5/1495 702/104 |
| 2013/0282302 A1 * | 10/2013 | Harper | G01D 18/00 702/21 |
| 2014/0156228 A1 * | 6/2014 | Molettiere | A61B 5/1118 702/189 |
| 2014/0163927 A1 * | 6/2014 | Molettiere | A61B 5/681 702/189 |
| 2014/0164611 A1 * | 6/2014 | Molettiere | H04L 67/22 709/224 |
| 2014/0365534 A1 * | 12/2014 | Bousamra | G06F 19/325 707/804 |
| 2015/0359490 A1 * | 12/2015 | Massey | A61B 5/4839 600/365 |

* cited by examiner

PHYSIOLOGICAL SENSOR HISTORY BACKFILL SYSTEM AND METHOD

RELATED APPLICATIONS

This application is a continuation application of U.S. patent application Ser. No. 14/304,686 filed Jun. 13, 2014 and issued on Feb. 27, 2018 as U.S. Pat. No. 9,901,305, which is herein incorporated by reference.

TECHNICAL FIELD

The technical field of this disclosure is personal physiological monitoring systems, particularly, physiological sensor history backfill systems and methods.

BACKGROUND OF THE INVENTION

Advances in electronics and telemetry have resulted in the miniaturization of medical devices such that medical devices which previously required large stationary equipment can now be worn about the person, who can be monitored or receive treatment while pursuing normal daily tasks.

One area of such advances has been in the treatment of diabetes. An estimated twenty-six million people in the United States, or about 8% of the population, have diabetes. This percentage is expected to increase in the near-term as the population ages. Wearable glucose monitors and insulin pumps have been developed which allow persons under treatment for diabetes to be monitored and receive insulin while carrying on their day-to-day tasks.

Current portable medical devices such as insulin pumps communicate with a glucose sensor/transmitter device that continuously monitors sensor activity over a radio frequency network. Small, compact continuous glucose monitors (CGMs) lack a user interface, so the CGMs send sensor information as readings to the insulin pump that provide user interfaces to allow the user to monitor these sensor information readings with graphs, icons, sensor alerts, selectable sensor readings, and statistical output. The insulin pump saves the sensor readings in a sensor history area that can be displayed to the user or downloaded to an external reporting application to provide the user and/or health care provider with a record of the insulin therapy delivered by the pump as reported by the CGM's sensor readings information.

Unfortunately, noise or interference which occurs when the CGM attempts to send sensor information to the insulin pump can prevent the insulin pump from receiving the information. Loss of power can also disable the CGM or insulin pump. This results in gaps in the sensor readings stored in the pump's sensor history area. Without this sensor information, the user interface is unable to provide the user or health care provider with a complete display of the patient history or a complete record of the results of the insulin therapy delivered by the pump.

It would be desirable to have a physiological sensor history backfill system and method that would overcome the above disadvantages.

SUMMARY OF THE INVENTION

One aspect of the invention provides a method of history backfill for a local base device operable to wirelessly communicate with a physiological sensor connected to a patient, the method including: obtaining physiological readings for the patient at a predetermined interval; storing the physiological readings at the physiological sensor as sensor physiological readings; storing the physiological readings at the local base device as historic physiological readings; obtaining a current physiological reading for the patient; transmitting the current physiological reading to the local base device in a current reading message; detecting a record gap in the historic physiological readings between the current physiological reading and the historic physiological readings; and filling the record gap in the historic physiological readings with sensor physiological readings from the physiological sensor when the current reading message does not include the sensor physiological readings to fill the record gap.

Another aspect of the invention provides a system of history backfill for a patient, the system including a physiological sensor and a local base device operable to wirelessly communicate with the physiological sensor. The physiological sensor has a processor and the memory operably coupled to the processor, the memory containing programming code executable by the processor to: obtain physiological readings for the patient; store the physiological readings at the physiological sensor as sensor physiological readings; transmit the physiological readings to the local base device; obtain a current physiological reading for the patient; transmit the current physiological reading in a current reading message to the local base device; receive a request for missing physiological readings; select sensor physiological readings for the missing physiological readings; and transmit the selected sensor physiological readings to the local base device. The local base device has a processing unit and a storage medium operably coupled to the processing unit, the storage medium containing programming code executable by the processing unit to: receive the physiological readings from the physiological sensor; store the physiological readings as historic physiological readings; receive the current physiological reading in the current reading message from the physiological sensor; detect a record gap in the historic physiological readings between the current physiological reading and the historic physiological readings; identify the missing physiological readings in the record gap; transmit the request for the missing physiological readings to the physiological sensor when the current reading message does not include the sensor physiological readings to fill the record gap; receive the selected sensor physiological readings from the physiological sensor; and fill the record gap with the selected sensor physiological readings.

Another aspect of the invention provides a method of history backfill for an insulin pump operable to wirelessly communicate with a glucose sensor connected to a patient, the method including: obtaining glucose readings for the patient at a predetermined interval, each of the glucose readings being associated with a glucose reading time; storing a predetermined storage number of the glucose readings at the glucose sensor with the associated glucose reading time, the predetermined storage number being greater than or equal to one and greater than a predetermined packet number; measuring a current glucose reading for the patient at a current measurement time; transmitting from the glucose sensor to the insulin pump a current message including the current glucose reading, the current measurement time, and the predetermined packet number of the glucose readings immediately before the current glucose reading, the predetermined packet number being greater than or equal to zero; retrieving a last stored glucose reading time from the insulin pump memory; calculating a time gap between the current measurement time and the last stored glucose reading time; setting a backfill start time equal to the last stored glucose reading time when the time gap is greater than a packet duration defined as the predetermined interval multiplied by the predetermined packet number; requesting the glucose sensor to transmit to the insulin pump the predetermined packet number of the glucose readings immediately after the backfill start time; storing the predetermined packet number of the glucose readings immediately after the backfill start time in the insulin pump; adding the packet duration to the backfill start time; and repeating the requesting, the storing, and the adding when a backfill end time defined as the backfill start time less the packet duration is less than the current measurement time.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
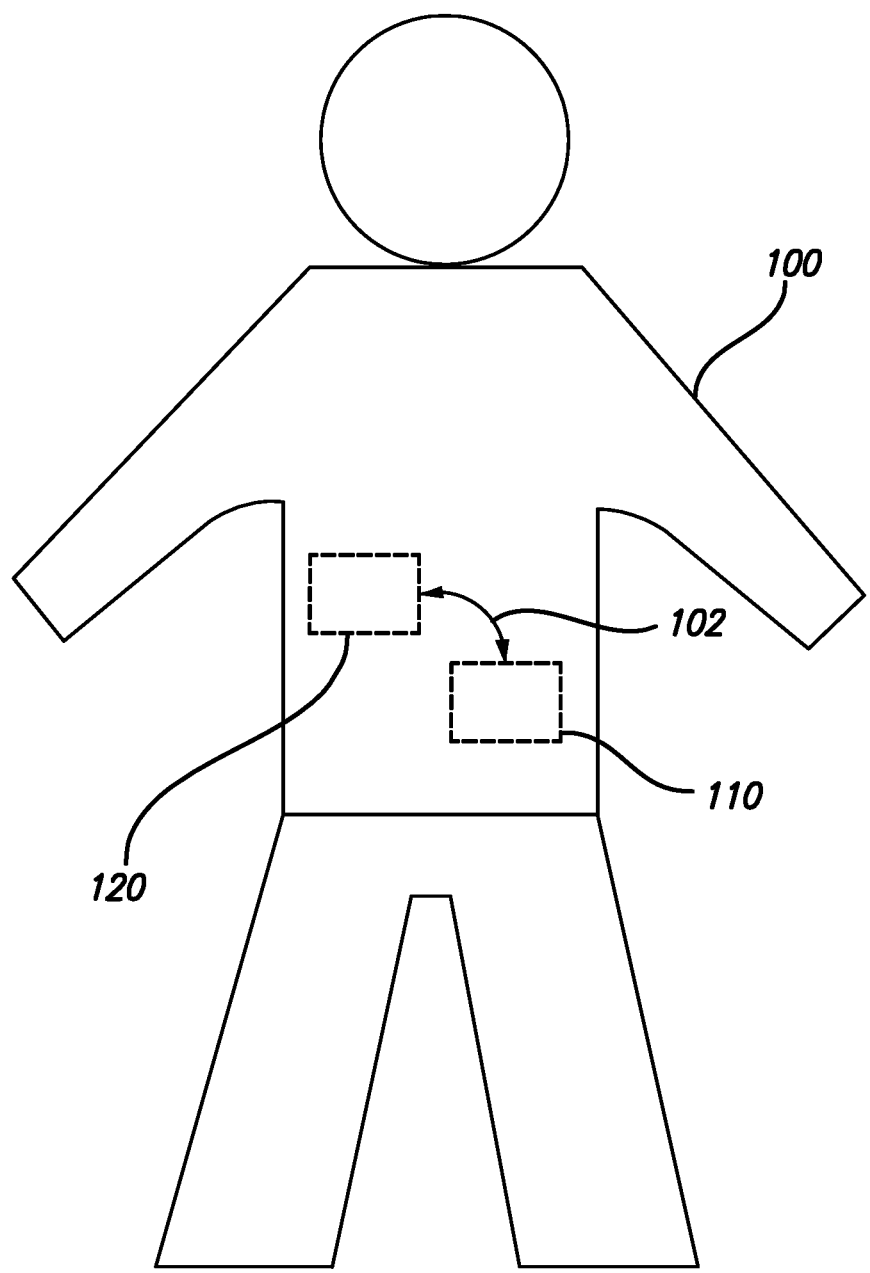
FIG. 1 is a schematic diagram of a physiological sensor and a local base device for a physiological sensor history backfill system in accordance with the invention.

FIG. 1 is a schematic diagram of a physiological sensor and a local base device for a physiological sensor history backfill system in accordance with the invention. In this example, the patient 100 is connected to a physiological sensor 110 and a local base device 120. The physiological sensor 110 is operable to wirelessly communicate with the local base device 120 across wireless link 102. Exemplary wireless links 102 include radio frequency connections, WiFi connections (such as Wi-Fi connections using 802.11b/g/n protocols), Bluetooth connections, and the like. In one embodiment, the physiological sensor 110 is a glucose sensor and the local base device 120 is an insulin pump.

The physiological sensor 110 can be any physiological sensor operable to obtain and store physiological readings for the patient. Exemplary physiological sensors 110 include glucose sensors, heart-rate sensors, ECG sensors, pulse oximeters, blood pressure sensors, respiration rate sensors, skin temperature sensors, electroencephalography (EEG) sensors, activity level sensors, vital sign sensors, and the like.

The local base device 120 can be any portable local base device carried by the patient to interact with the physiological sensor 110 and to store physiological readings. Exemplary local base devices 120 include insulin pumps, cell pumps, local monitors, fitness monitors, smart phones, portable/wearable computing devices, watches, tablets, computers, and the like. The local base device 120 can optionally communicate with remote locations over cellular communication networks or the like so that medical personnel or the like can download and analyze the physiological readings.

Figure 2:
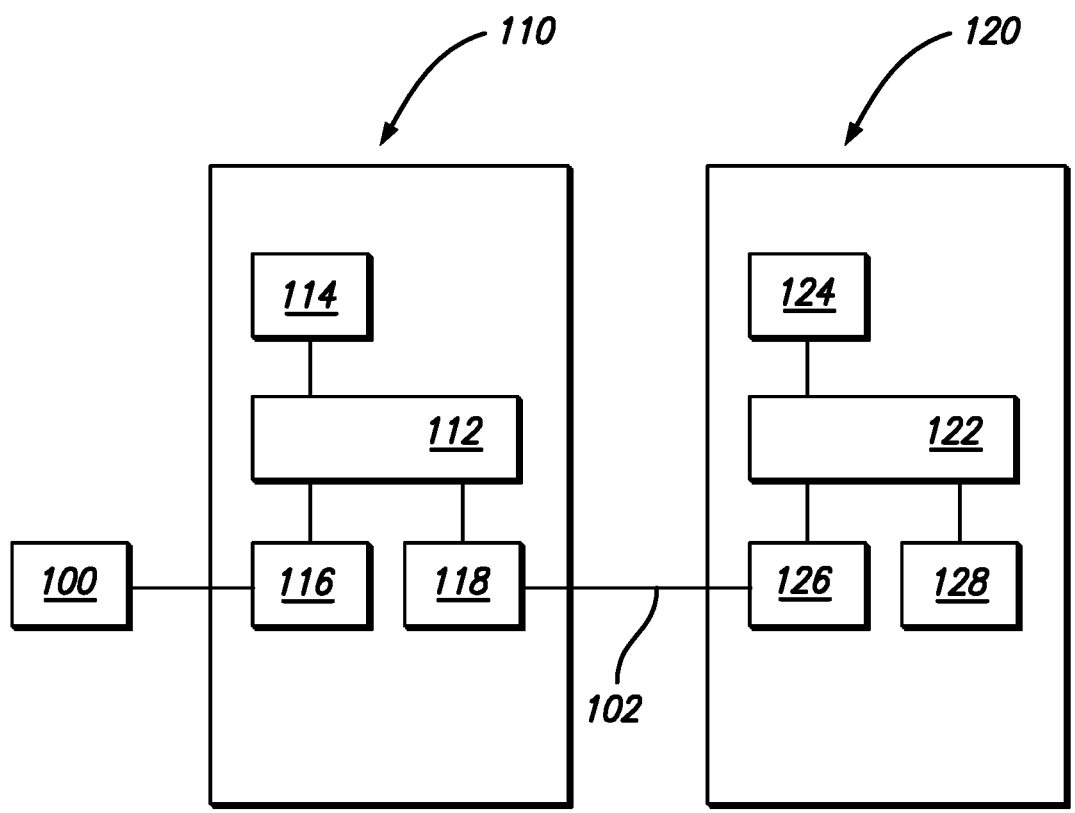
FIG. 2 is a block diagram of a physiological sensor and a local base device for a physiological sensor history backfill system in accordance with the invention.

FIG. 2, in which like elements share like element numbers with FIG. 1, is a block diagram of a physiological sensor and a local base device for a physiological sensor history backfill system in accordance with the invention. The physiological sensor 110 can include processor 112, and operably coupled to the processor 112, memory 114, sensor 116, and transmitter/receiver 118. The local base device 120 can include processing unit 122, and operably coupled to the processing unit 122, storage medium 124, transmitter/receiver 126, and optional user I/O interface 128.

For the physiological sensor 110, the sensor 116 obtains physiological readings from the patient 100. The physiological readings can be stored in the memory 114 as sensor physiological readings. The memory 114 can also store programming code executable by the processor 112. The physiological readings can also be transmitted through the transmitter/receiver 118 to the local base device 120 over the wireless link 102.

For the local base device 120, the transmitter/receiver 126 can receive physiological readings from the physiological sensor 110 and store the physiological readings as historic physiological readings in the storage medium 124. The storage medium 124 can also store programming code executable by the processing unit 122. The patient 100 can use the optional user I/O interface 128 to provide input to and receive information from the local base device 120.

In one embodiment, the memory 114 of the physiological sensor 110 contains programming code executable by the processor 112 to: obtain physiological readings for the patient; store the physiological readings at the physiological sensor as sensor physiological readings; transmit the physiological readings to the local base device; obtain a current physiological reading for the patient; transmit the current physiological reading in a current reading message to the local base device; receive a request for missing physiological readings; select sensor physiological readings for the missing physiological readings; and transmit the selected sensor physiological readings to the local base device.

In one embodiment, the storage medium 124 of the local base device 120 contains programming code executable by the processing unit 122 to: receive the physiological readings from the physiological sensor; store the physiological readings as historic physiological readings; receive the current physiological reading in the current reading message from the physiological sensor; detect a record gap in the historic physiological readings between the current physiological reading and the historic physiological readings; identify the missing physiological readings in the record gap; transmit the request for the missing physiological readings to the physiological sensor when the current reading message does not include the sensor physiological readings to fill the record gap; receive the selected sensor physiological readings from the physiological sensor; and fill the record gap with the selected sensor physiological readings.

Figure 3:
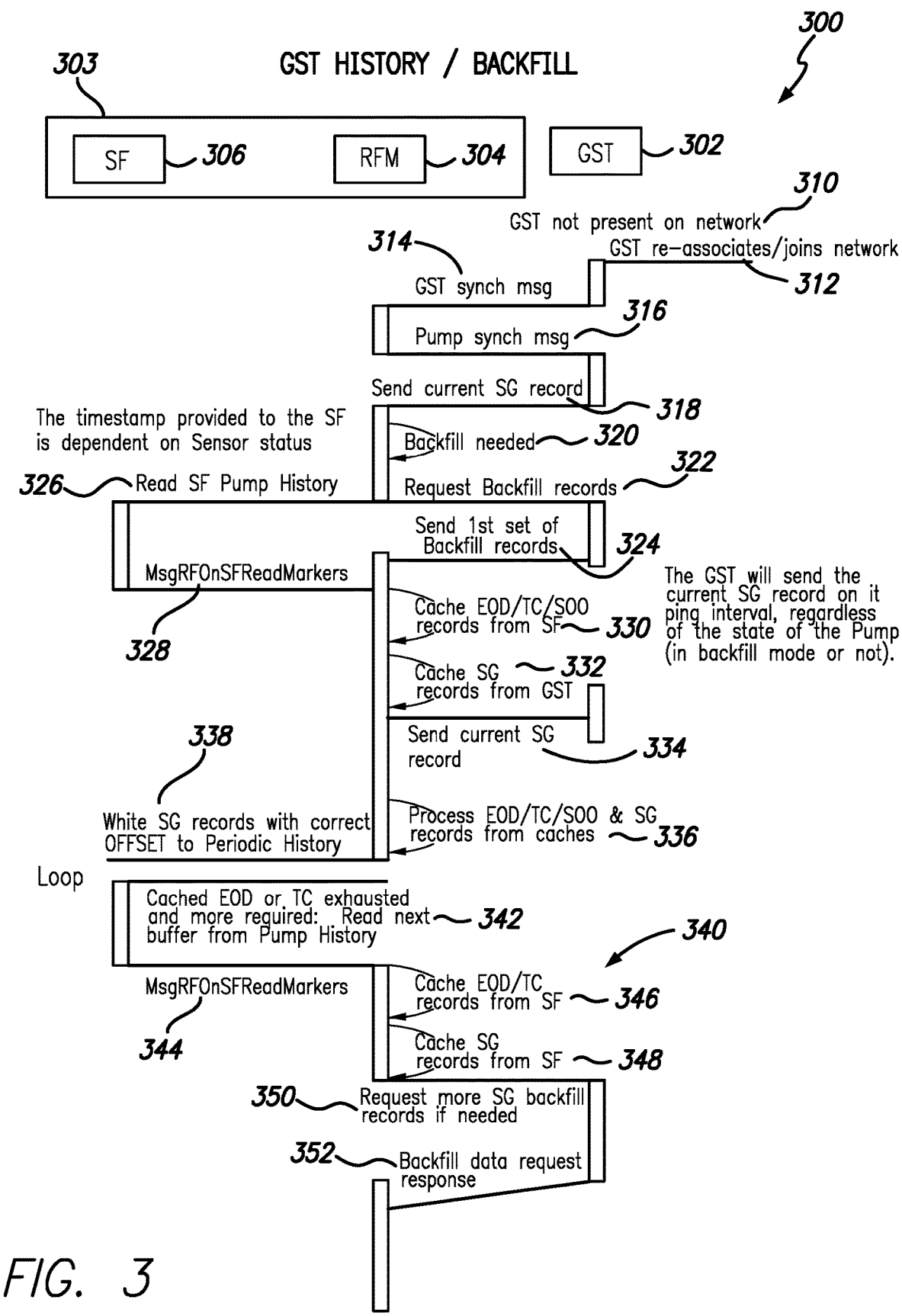
FIG. 3 is a timing/event chart for physiological sensor history backfill in accordance with the invention.

FIG. 3 is a timing/event chart for physiological sensor history backfill in accordance with the invention. In this example, the local base device is an insulin pump and the physiological sensor is a glucose sensor connected to the patient, the insulin pump being operable to wirelessly communicate with the glucose sensor.

The timing/event chart 300 illustrates timing and events for a glucose sensor 302 connected to a patient. An insulin pump 303 is operable to wirelessly communicate with the glucose sensor 302 and includes a processing unit 304 in communication with a storage medium 306 storing data and instructions for the insulin pump 303.

At 310, in this example, the glucose sensor 302 is not in wireless communication with the insulin pump 303. The lack of wireless communication can be caused by noise or interference near the patient, with the result that the glucose readings for the patient measured at the glucose sensor 302 did not reach the insulin pump 303. Because the insulin pump 303 is not receiving the glucose readings, a record gap develops in the historic glucose readings stored in the insulin pump 303.

At 312, wireless communication between the glucose sensor 302 and the insulin pump 303 is restored. The glucose sensor 302 sends a glucose sensor time sync message 314 to the processing unit 304, which returns an insulin pump time sync message 316 to the glucose sensor 302. The optional synchronization procedure synchronizes the insulin pump clock with the glucose sensor clock after restoration of wireless communication. Even though the time sync is optional here, in one embodiment, the insulin pump can require the timestamp for each current glucose sensor reading to be within 2 seconds of the insulin pump timestamp.

The glucose sensor 302 sends a current reading message 318 including a current glucose reading for the patient to the processing unit 304. In one example, the current reading message can include the current glucose reading, the current measurement time, and a predetermined packet number of glucose readings immediately before the current glucose reading. In one example, the predetermined packet number of the glucose readings is eight glucose readings, but any number greater than or less than eight may be utilized according to embodiments of the present invention. The current measurement time provides an accurate time for each current reading message.

At 320, the processing unit 304 determines whether there is a record gap in the historic glucose readings stored in the storage medium 306 such that sensor history backfill is required. In one embodiment, the processing unit 304 determines that there is a record gap by retrieving a last stored glucose reading time from the storage medium 306; and calculating a time gap between the current measurement time and the last stored glucose reading time. When the current reading message includes enough sensor glucose readings to fill the record gap, there is no need to obtain additional sensor glucose readings, since the current reading message already includes enough information to complete the historic record.

When the processing unit 304 determines that there is a record gap in the historic glucose readings such that sensor history backfill is required, the processing unit 304 sends a backfill record request 322 starting with the last stored glucose reading time to the glucose sensor 302. In response at 324, the glucose sensor 302 returns a first predetermined packet number of the glucose readings following the last stored glucose reading time. In one example, the predetermined packet number of the glucose readings is eight glucose readings, but any number greater than or less than eight may be utilized according to embodiments of the present invention.

When the processing unit 304 determines that there is a record gap in the historic glucose readings such that sensor history backfill is required, the processing unit 304 can also send a pump history data request 326 to the storage medium 306. In response, the storage medium 306 returns pump history data 328 following the last stored glucose reading time. The pump history data 328 can include markers for events that occurred during the record gap, such as the patient making a time change at the insulin pump 303 (Time Change marker), the patient manually turning off/on the glucose sensor (Sensor Off marker, Sensor On marker), changing of the day through the passage of time (Start of Day marker, End of Day marker), and the like. At 330, the processing unit 304 detects the event markers and caches the event markers at the insulin pump 303. At 332, the processing unit 304 caches the predetermined packet number of the glucose readings at the insulin pump 303. The cached glucose readings fall within the time interval of the pump history data 328. The caching of the predetermined packet number of the glucose readings takes advantage of the pump history data structure which allows up to eight glucose readings to be written at a time.

At 334, the glucose sensor 302 transmits the glucose reading normally obtained for the patient at the predetermined interval to the insulin pump 303. Thus, the normal procedure of obtaining glucose readings and storing them at the glucose sensor and insulin pumps can continue during the sensor history backfill procedure. Those skilled in the art will appreciate that the normal procedure can be maintained or suspended during the sensor history backfill procedure as desired for a particular application.

At 336, the processing unit 304 processes the cached event markers and cached glucose readings, so that each glucose reading being backfilled to the storage medium 306 is associated with the time on the user clock (the local time at the patient's location as entered by the patient) at which the glucose reading was obtained. At 338, the processing unit 304 stores the backfill records in the storage medium 306 as historic glucose readings. The first backfill record is stored immediately adjacent to the record at the last stored glucose reading time.

The backfill procedure continues until the record gap is filled as indicated in the loop portion 340 of the timing/event chart 300. At 342, the processing unit 304 sends another pump history data request to the storage medium 306, after determining that the cached event markers have all been used. In response, the storage medium 306 returns pump history data 344 for the next portion of the record gap to be filled.

At 346, the processing unit 304 detects the event markers and caches the event markers at the insulin pump 303. At 348, the processing unit 304 caches the glucose readings at the insulin pump 303. The cached glucose readings fall within the time interval of the pump history data 348.

When additional stored glucose readings are required from the glucose sensor 302, i.e., when the cached glucose readings have all been used, the processing unit 304 sends a backfill record request 350 to the glucose sensor 302. In response at 352, the glucose sensor 302 returns an additional predetermined packet number of the glucose readings. The loop portion 340 of the timing/event chart 300 can be repeated until the record gap is filled.

Figure 4:
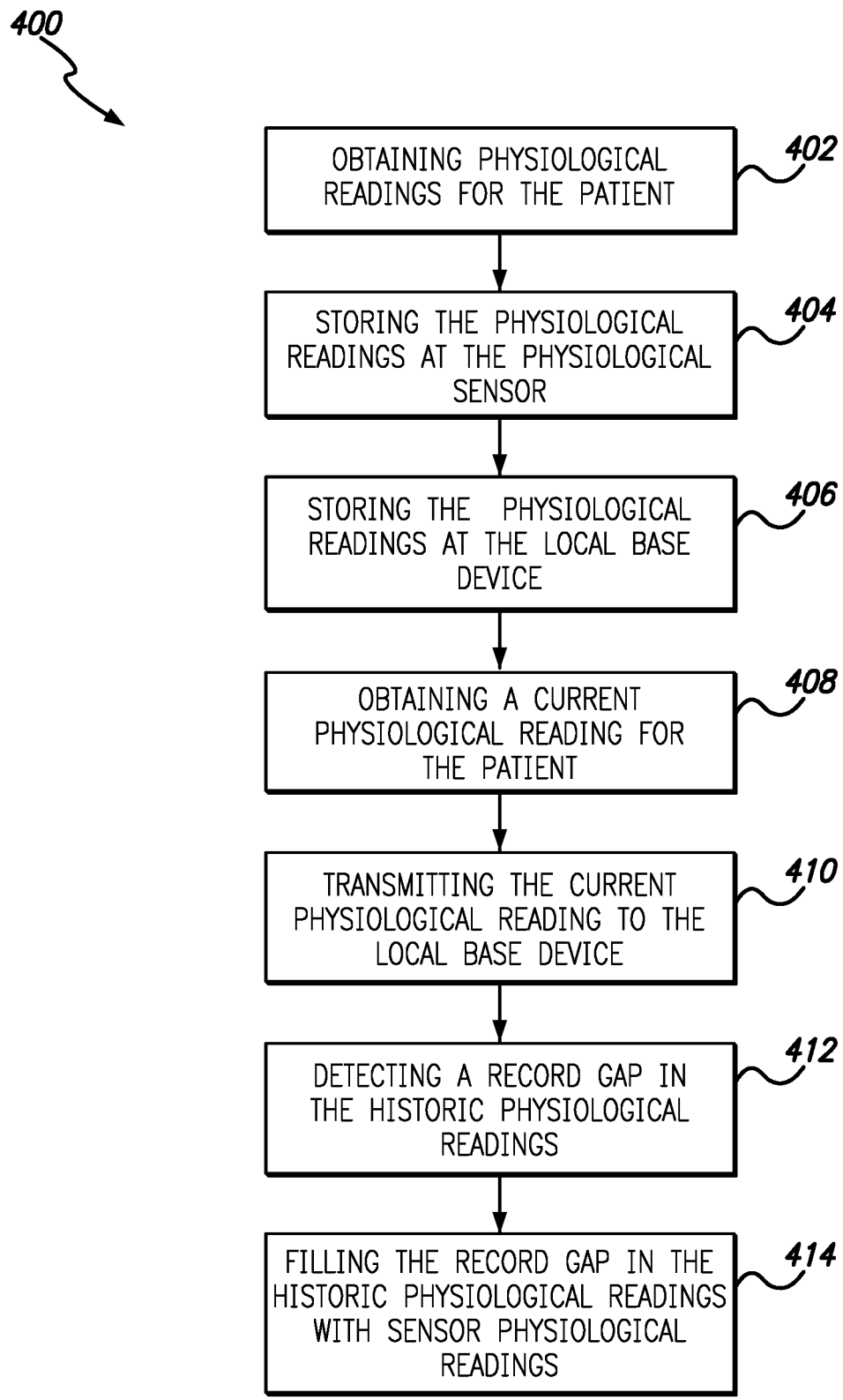
FIG. 4 is a flow chart of a method of physiological sensor history backfill in accordance with the invention.

FIG. 4 is a flow chart of a method of personal physiological sensor history backfill in accordance with the invention. The method 400 for a local base device operable to wirelessly communicate with a physiological sensor connected to a patient includes obtaining physiological readings for the patient 402 at a predetermined interval; storing the physiological readings at the physiological sensor 404 as sensor physiological readings; storing the physiological readings at the local base device 406 as historic physiological readings; obtaining a current physiological reading for the patient 408; transmitting the current physiological reading to the local base device 410 in a current reading message; detecting a record gap in the historic physiological readings 412 between the current physiological reading and the historic physiological readings; and filling the record gap in the historic physiological readings with sensor physiological readings 414 from the physiological sensor when the current reading message does not include the sensor physiological readings to fill the record gap.

Once the record gap has been filled, the historic physiological readings can be presented in a number of ways on the local base device, such as in a graph of physiological readings over several selectable periods of time, e.g., 3, 6, 12, 24 hours, including color coding of data that has been received in real time or has been backfilled; an icon depicting whether the expected sensor information has been received; sensor alerts based on high and/or low limits requested by the user; historic display of readings by day or selected days; summaries of sensor statistics over a selected time period; and the like. The reconstructed historic physiological readings provide the user and health care provider with an accurate record of the user's physiological data.

The method 400 can be carried out on a variable data usage personal medical system as described for FIGS. 1 & 2. Referring to FIG. 4, in one embodiment, the local base device and physiological sensor in the method 400 are an insulin pump and a glucose sensor, respectively. In one embodiment, the local base device includes a local base device clock and the physiological sensor includes a physiological sensor clock, and the method 400 further includes synchronizing the local base device clock and the physiological sensor clock before the transmitting the current physiological reading to the local base device 410 in a current reading message.

Obtaining physiological readings for the patient 402 at a predetermined interval can include obtaining physiological readings from any physiological sensor connected to the patient and sensing a physiological parameter. Exemplary physiological sensors include glucose sensors, heart-rate sensors, ECG sensors, pulse oximeters, blood pressure sensors, respiration rate sensors, skin temperature sensors, electroencephalography (EEG) sensors, activity level sensors, vital sign sensors, and the like. Those skilled in the art will appreciate that the physiological sensor can be any sensor desired for a particular application. The predetermined interval can be selected as desired for a particular application. In one embodiment, the predetermined interval can be five minutes.

Storing the physiological readings at the physiological sensor 404 as sensor physiological readings can include storing the physiological readings in flash memory included in the physiological sensor. In one embodiment, the flash memory can store ten hours of physiological readings.

Storing the physiological readings at the local base device 406 as historic physiological readings can include storing the physiological readings in flash memory included in the local base device. In one embodiment, the flash memory can store thirty days of physiological readings. Exemplary local base devices include insulin pumps, cell pumps, local monitors, fitness monitors, smart phones, portable/wearable computing devices, watches, tablets, computers, and the like.

Obtaining a current physiological reading for the patient 408 can include obtaining the current physiological reading regardless of whether the physiological sensor is able to communicate wirelessly with the local base device. In one embodiment, storing the physiological readings at the local base device 406 may not have been possible before obtaining the current physiological reading because the wireless link between the physiological sensor and the local base device was not available.

Transmitting the current physiological reading to the local base device 410 in a current reading message can include transmitting the current physiological reading to the local base device after an interrupted wireless link between the physiological sensor and the local base device has been restored.

Detecting a record gap in the historic physiological readings 412 between the current physiological reading and the historic physiological readings can include determining at the local base device whether there is a time gap between the current measurement time at which the current physiological reading was taken at the physiological sensor and the last stored glucose reading time for the most recent historic physiological reading. The time gap can occur from an interruption in the wireless link between the physiological sensor and the local base device, during which time the local base devices are unable to receive physiological readings for storage.

Filling the record gap in the historic physiological readings with sensor physiological readings 414 from the physiological sensor occurs when the current reading message does not include the sensor physiological readings to fill the record gap. In one embodiment, the current reading message can include information in addition to the current physiological reading. In one example, the current reading message can include the current physiological reading, the current measurement time, and a predetermined packet number of physiological readings immediately before the current physiological reading. When the current reading message includes enough sensor physiological readings to fill the record gap, there is no need to obtain additional sensor physiological readings, since the current reading message already includes enough information to complete the historic record. For example, when the record gap is missing six historic physiological readings and the current reading message includes eight physiological readings immediately before the current physiological reading, the six physiological readings in the current reading message immediately before the current physiological reading can be used to fill the record gap.

When the current reading message does not include the sensor physiological readings to fill the record gap, additional sensor physiological readings can be obtained from the physiological sensor to fill the record gap. For example, when the record gap is missing a twelve historic physiological readings and the current reading message includes eight physiological readings immediately before the current physiological reading, the first eight physiological readings in the current reading message can be used to fill part of the record gap, but a record gap of four historic physiological readings remains. The four historic physiological readings can be obtained from the physiological sensor to fill the remainder of the record gap. In one embodiment, filling the record gap in the historic physiological readings with sensor physiological readings 414 can further include repeatedly transferring a predetermined packet number of sensor physiological readings from the physiological sensor to the local base device to provide the sensor physiological readings required to fill the record gap.

Filling the record gap in the historic physiological readings with sensor physiological readings 414 can also account for additional events that occurred during the time gap. Exemplary events include the patient making a time change at the local base device, the patient manually turning off/on the sensor, changing of the day through the passage of time, and the like.

In one embodiment, filling the record gap in the historic physiological readings with sensor physiological readings 414 further includes detecting a Time Change marker that occurred during the record gap, the Time Change marker being stored at the local base device; and adjusting a user clock associated with the historic physiological readings in the record gap on and after a time of the Time Change marker by a time change value associated with the Time Change marker. The local base device can keep a user clock that is the local time at the patient's location as entered by the patient. The Time Change marker stored in the local base device indicates that the patient has changed the time. For example, when the patient travels from the western time zone to the central time zone in the United States, the patient can adjust the user clock by two hours to account for the time difference: a Time Change marker is stored in the local base device with the associated time the user clock adjustment is made, along with an associated time change value. When the Time Change marker appears during the record gap, the time for the sensor physiological readings used to fill the record gap on or after the time the user clock adjustment was made can be adjusted by the time change value.

In one embodiment, filling the record gap in the historic physiological readings with sensor physiological readings 414 further includes detecting a Sensor Off marker that occurred during the record gap, the Sensor Off marker being stored at the local base device; and assigning a Sensor Off value to the historic physiological readings in the record gap on and after a time of the Sensor Off marker. The patient can turn the sensor off whenever they like, so that no data is recorded. Any readings received by the local base device from the physiological sensor when the patient has turned the sensor off are discarded and not processed. The Sensor Off marker stored in the local base device indicates that the patient has turned off the sensor. For example, when the patient has a meeting and does not want to be interrupted by the local base device, or the patient is in an area such as an airplane where no radio frequency transmission is permitted, the patient can turn off the sensor. When the Sensor Off marker appears during the record gap, the Sensor Off value can be used to fill the record gap on or after the time the sensor was turned off, so that no numerical value appears for those historic physiological readings. In one embodiment, a separate Sensor Off value is assigned to and stored for each of the historic physiological readings in the record gap in separate memory locations on and after a time of the Sensor Off marker. In another embodiment, a single Sensor Off value is assigned to and stored across all the historic physiological readings in the record gap in one memory location on and after a time of the Sensor Off marker, reducing the amount of storage required.

The method 400 can continue when the patient turns on the sensor. In one embodiment, filling the record gap in the historic physiological readings with sensor physiological readings 414 further includes detecting a Sensor On marker that occurred during the record gap, the Sensor On marker being stored at the local base device; and filling the record gap in the historic physiological readings in the record gap after a time of the Sensor On marker with sensor physiological readings from the physiological sensor. When the Sensor On marker appears during the record gap, a special gap record is saved indicating no sensor readings were written since the timestamp of the previously saved reading until the timestamp for the gap record; subsequent sensor physiological readings from the physiological sensor can be used to fill the record gap on or after the time the sensor was turned on.

In one embodiment, filling the record gap in the historic physiological readings with sensor physiological readings 414 further includes accounting for End of Day markers, which allows accurate retrieval and graphing of the records for a particular date. In one embodiment, the filling 414 further includes detecting an End of Day marker that occurred during the record gap, the End of Day marker being stored at the local base device; and associating the End of Day marker with the historic physiological readings in the record gap at a time of the End of Day marker. Thus, the End of Day markers are integrated into the backfilled historic physiological readings ordered on the basis of their time of occurrence.

Start of Day (SOD) and End of Day (EOD) markers are saved in the sensor history area as they occur on the local base device, and define the day boundaries used to retrieve and display or graph sensor physiological readings requested by the user for a specific date. When sensor physiological readings arrive at their expected periodic interval and are saved in the sensor history area of the local base device, i.e., during normal operation, the SOD and EOD markers are also saved in the sensor history area of the local base device at the time they occur to define the day boundaries used for daily history retrieval of the sensor physiological readings. When the sensor physiological readings have not arrived as expected and are late when an EOD event occurs, e.g., when communication has been lost between the local base device and the physiological sensor, an EOD marker is not saved in sensor history of the local base device, but is stored elsewhere in the local base device for later EOD marker processing when the stored EOD marker can be written in an integrated manner with the backfilled sensor physiological readings. This allows the daily history retrieval of sensor physiological information to accurately be presented to the user when requested.

The method 400 can also account for situations in which the number of missing historic physiological readings in the record gap is greater than the number of sensor physiological readings available in the physiological sensor. In one embodiment, filling the record gap in the historic physiological readings with sensor physiological readings 414 further includes assigning a Gap Fill value to the historic physiological readings in the record gap before a fillable start time defined as time of the current physiological reading less a maximum physiological sensor storage time. For example, when the record gap is 12 hours and the maximum physiological sensor storage time is 10 hours of physiological readings, the Gap Fill value can be used to fill the record gap from the beginning of the record gap until the fillable start time two hours later, so that it is apparent that no numerical values are available for those historic physiological readings.

The method 400 can also account for errors which occur during sensor history backfill. When the pump history data is corrupted, as indicated by cyclic redundancy check (CRC) error when reading the pump history data from the storage medium, the insulin pump aborts the sensor history backfill. When a block of the pump history data is not a completely written (unclosed) because of an unexpected reset, the insulin pump aborts the sensor history backfill. When a block of the pump history data is unexpectedly empty, the insulin pump aborts the sensor history backfill. When a block signature (CRC and datalength) are both zero indicating a bad CRC on the original write with no data loss, the block with the bad block signature is ignored and the sensor history backfill continues with reading the next block. When the pump history data is corrupted, as indicated by cyclic redundancy check (CRC) error when reading the pump history data delivered to the processing unit, the insulin pump aborts the sensor history backfill. When the insulin pump aborts the sensor history backfill, the pump history data in the storage medium can be returned to a condition to preserve the integrity of subsequent data searching and retrieval. In one embodiment, the insulin pump can save critical data required for sensor history backfill to nonvolatile memory, so that the data history backfill can continue from the point of interruption when the insulin pump resets during sensor history backfill.

The method 400 can be applied as discussed below when the local base device is an insulin pump and the physiological sensor is a glucose sensor connected to the patient, the insulin pump being operable to wirelessly communicate with the glucose sensor.

Obtaining physiological readings for the patient 402 at a predetermined interval can include obtaining glucose readings for the patient at a predetermined interval, each of the glucose readings being associated with a glucose reading time.

Storing the physiological readings at the physiological sensor 404 as sensor physiological readings can include storing a predetermined storage number of the glucose readings at the glucose sensor with the associated glucose reading time, the predetermined storage number being greater than or equal to one and greater than a predetermined packet number.

Obtaining a current physiological reading for the patient 408 can include measuring a current glucose reading for the patient at a current measurement time.

Transmitting the current physiological reading to the local base device 410 in a current reading message can include transmitting from the glucose sensor to the insulin pump a current message including the current glucose reading, the current measurement time, and the predetermined packet number of the glucose readings immediately before the current glucose reading, the predetermined packet number being greater than or equal to zero.

Detecting a record gap in the historic physiological readings 412 between the current physiological reading and the historic physiological readings can include retrieving a last stored glucose reading time from the insulin pump memory; and calculating a time gap between the current measurement time and the last stored glucose reading time.

Filling the record gap in the historic physiological readings with sensor physiological readings 414 from the physiological sensor when the current reading message does not include the sensor physiological readings to fill the record gap can include setting a backfill start time equal to the last stored glucose reading time when the time gap is greater than a packet duration defined as the predetermined interval multiplied by the predetermined packet number; requesting the glucose sensor to transmit to the insulin pump the predetermined packet number of the glucose readings immediately after the backfill start time; storing the predetermined packet number of the glucose readings immediately after the backfill start time in the insulin pump; adding the packet duration to the backfill start time; and repeating the requesting, the storing, and the adding when a backfill end time defined as the backfill start time less the packet duration is less than the current measurement time.

It is important to note that FIGS. 1-4 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A method of sensor history backfill for a local base device operable to wirelessly communicate with a physiological sensor connected to a patient, the method comprising:
   obtaining physiological readings for the patient at a predetermined interval;
   storing the physiological readings at the physiological sensor as sensor physiological readings;
   transmitting the physiological readings from the physiological sensor to the local base device;
   storing the physiological readings at the local base device as historic physiological readings;
   obtaining a current physiological reading for the patient;
   transmitting the current physiological reading from the physiological sensor to the local base device in a current reading message;
   detecting at the local base device a record gap in the historic physiological readings between the current physiological reading and the historic physiological readings;
   identifying missing physiological readings in the record gap;
   transmitting a request for the missing physiological readings from the local base device to the physiological sensor when the current reading message does not include the sensor physiological readings to fill the record gap;
   selecting sensor physiological readings for the missing physiological readings;
   transmitting the selected sensor physiological readings from the physiological sensor to the local base device; and
   filling the record gap in the historic physiological readings with the selected sensor physiological readings from the physiological sensor.

2. The method of claim 1 wherein the local base device is an insulin pump and the physiological sensor is a glucose sensor.

3. The method of claim 1 wherein the local base device includes a local base device clock and the physiological sensor includes a physiological sensor clock, the method further comprising synchronizing the local base device clock and the physiological sensor clock before transmitting the current physiological reading from the physiological sensor to the local base device in the current reading message.

4. The method of claim 1 wherein the filling further comprises repeatedly transferring a predetermined packet number of sensor physiological readings from the physiological sensor to the local base device to provide the sensor physiological readings required to filling the record gap.

5. The method of claim 1 wherein the filling further comprises:
   detecting a Time Change marker that occurred during the record gap, the Time Change marker being stored at the local base device; and
   adjusting a user clock associated with the historic physiological readings in the record gap on and after a time of the Time Change marker by a time change value associated with the Time Change marker.

6. The method of claim 1 wherein the filling further comprises:
detecting a Sensor Off marker that occurred during the record gap, the Sensor Off marker being stored at the local base device; and
assigning a Sensor Off value to the historic physiological readings in the record gap on and after a time of the Sensor Off marker.

7. The method of claim 1 wherein the filling further comprises:
detecting a Sensor On marker that occurred during the record gap, the Sensor On marker being stored at the local base device; and
filling the record gap in the historic physiological readings in the record gap after a time of the Sensor On marker with sensor physiological readings from the physiological sensor.

8. The method of claim 1 wherein the filling further comprises:
detecting an End of Day marker that occurred during the record gap, the End of Day marker being stored at the local base device; and
associating the End of Day marker with the historic physiological readings in the record gap at a time of the End of Day marker.

9. The method of claim 1 wherein the filling further comprises:
assigning a Gap Fill value to the historic physiological readings in the record gap before a fillable start time defined as time of the current physiological reading less a maximum physiological sensor storage time.

10. The method of claim 1, further comprising:
detecting an error during sensor history backfill; and
aborting the filling in response to detecting the error.

11. A method of sensor history backfill for a local base device operable to wirelessly communicate with a physiological sensor connected to a patient, the method comprising:
obtaining physiological readings for the patient at a predetermined interval, each of the physiological readings being associated with a physiological reading time;
storing a predetermined storage number of the physiological readings at the physiological sensor with the associated physiological reading time, the predetermined storage number being greater than or equal to one and greater than a predetermined packet number;
measuring a current physiological reading for the patient at a current measurement time;
transmitting from the physiological sensor to the local base device a current message including the current physiological reading, the current measurement time, and the predetermined packet number of the physiological readings immediately before the current physiological reading, the predetermined packet number being greater than or equal to zero;
retrieving a last stored physiological reading time from the local base device memory;
calculating a time gap between the current measurement time and the last stored physiological reading time;
setting a backfill start time equal to the last stored physiological reading time when the time gap is greater than a packet duration defined as the predetermined interval multiplied by the predetermined packet number;
requesting the physiological sensor to transmit to the local base device the predetermined packet number of the physiological readings immediately after the backfill start time;
storing the predetermined packet number of the physiological readings immediately after the backfill start time in the local base device;
adding the packet duration to the backfill start time; and
repeating the requesting, the storing, and the adding when a backfill end time defined as the backfill start time less the packet duration is less than the current measurement time.

12. The method of claim 11 wherein the local base device is an insulin pump and the physiological sensor is a glucose sensor.

13. The method of claim 11 wherein the local base device includes a local base device clock and the physiological sensor includes a physiological sensor clock, the method further comprising synchronizing the local base device clock and the physiological sensor clock before transmitting the current physiological reading from the physiological sensor to the local base device in the current reading message.

14. The method of claim 11, further comprising:
detecting a Time Change marker that occurred during the time gap, the Time Change marker being stored at the local base device; and
adjusting a user clock associated with physiological readings stored at the local base device on and after a time of the Time Change marker by a time change value associated with the Time Change marker.

15. The method of claim 11, further comprising:
detecting a Sensor Off marker that occurred during the time gap, the Sensor Off marker being stored at the local base device; and
assigning a Sensor Off value to physiological readings stored at the local base device on and after a time of the Sensor Off marker.

16. The method of claim 11, further comprising:
detecting a Sensor On marker that occurred during the time gap, the Sensor On marker being stored at the local base device; and
filling the time gap after a time of the Sensor On marker with sensor physiological readings from the physiological sensor.

17. The method of claim 11, further comprising:
detecting an End of Day marker that occurred during the time gap, the End of Day marker being stored at the local base device; and
associating the End of Day marker with physiological readings stored at the local base device at a time of the End of Day marker.

18. The method of claim 11, further comprising:
assigning a Gap Fill value to physiological readings stored at the local base device before a fillable start time defined as time of the current physiological reading less a maximum physiological sensor storage time.

19. The method of claim 11, further comprising:
detecting an error during sensor history backfill; and
aborting the filling in response to detecting the error.

* * * * *